United States Patent
Monneret et al.

(10) Patent No.: US 7,378,419 B2
(45) Date of Patent: May 27, 2008

(54) 9-AMINO-PODOPHYLLOTOXIN DERIVATIVES, METHOD FOR THE PRODUCTION THEREOF AND PHARMACEUTICAL COMPOSITIONS CONTAINING SAID DERIVATIVES

(75) Inventors: Claude Monneret, Paris (FR); Daniel Dauzonne, Paris (FR); John Hickman, Paris (FR); Alain Pierre, Les Alluets le Roi (FR); Laurence Kraus-Berthier, Colombes (FR); Bruno Pfeiffer, Saint Leu la Foret (FR); Pierre Benard, Le Chesnay (FR)

(73) Assignees: Les Laboratoires Servier, Seine (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 10/576,201

(22) PCT Filed: Sep. 1, 2004

(86) PCT No.: PCT/FR2004/002218

§ 371 (c)(1),
(2), (4) Date: Apr. 17, 2006

(87) PCT Pub. No.: WO2005/023817

PCT Pub. Date: Mar. 17, 2005

(65) Prior Publication Data

US 2006/0247246 A1    Nov. 2, 2006

(30) Foreign Application Priority Data

Sep. 2, 2003   (FR) .................................. 03 10367

(51) Int. Cl.
   - C07D 405/00  (2006.01)
   - A61K 31/50  (2006.01)
   - A01N 43/36  (2006.01)

(52) U.S. Cl. ............... 514/252.01; 514/423; 548/526

(58) Field of Classification Search ........... 514/252.01, 514/423; 548/526
See application file for complete search history.

(56) References Cited

U.S. PATENT DOCUMENTS

| 3,634,459 A | 1/1972 | von Wartburg et al. |
| 5,536,847 A | 7/1996 | Terada et al. |
| 5,541,223 A | 7/1996 | Lee et al. |
| 6,566,393 B1* | 5/2003 | Lee et al. ............. 514/463 |
| 2003/0032625 A1* | 2/2003 | Jensen et al. ........... 514/79 |

FOREIGN PATENT DOCUMENTS

| WO | WO-90/09788 | 9/1990 |
| WO | WO-97/13776 | 4/1997 |

OTHER PUBLICATIONS

Cho et al. J. Med. Chem., 1996, 36, 1383-1395.*
Carmichael et al.; "Evaluation of a Tetrazolium-Based Semiautomated Colorimetric Assay: Assessment of Chemosensitivity Testing"; Cancer Research, vol. 47, pp. 936-942, Feb. 15, 1987.
Cho et al.; "Antitumor Agents. 163. Three-Dimensional Quantitative Structure-Activity Relationship Study of 4'-O-Demethylepipodophyllotoxin Analogs Using the Modified CoMFA/$q^2$-GRS Approach"; J. Med. Chem. vol. 39, pp. 1383-1395, (1996).

* cited by examiner

*Primary Examiner*—Kamal A. Saeed
*Assistant Examiner*—Robert Havlin
(74) *Attorney, Agent, or Firm*—Foley & Lardner LLP

(57) ABSTRACT

The invention relates to compounds of formula (I), wherein $R_1$ is a group selected from hydrogen, alkyl, aryl, aryalkil, heteroaryl, heteroarylalkyl, alkylcarbonyl, arylcarbonyl, arylalkylcarbonyl, alkoxycarbonyl, aryloxycarbonyl, arylalkoxycarbonyl, heterocycloalkoxycarbonyl, alkylsulfonyl, arylsulfonyl, arylalkylsulfonyl, phosphonic and $Si(R_a)_2R_b$, Y is a group selected from HN—NH and N—$R_2$, $R_3$ is a hydrogen atom, an alkyl, cycloalkyl, aryl, arylalkyl group, $R_4$ is hydrogen atom or an alkyl group, enantiomers, diastereoisomers and the salts thereof 13 Claims, No Drawings

9-AMINO-PODOPHYLLOTOXIN DERIVATIVES, METHOD FOR THE PRODUCTION THEREOF AND PHARMACEUTICAL COMPOSITIONS CONTAINING SAID DERIVATIVES

The present invention relates to novel 9-aminopodophyllotoxin derivatives, a method for the preparation thereof and pharmaceutical compositions containing said derivatives.

The compounds of the invention constitute podophyllotoxin derivatives, a natural lignan known for its utility in the treatment of cancer. Others synthetic derivatives such as etoposide and teniposide are used currently as chemotherapeutic agents for the treatment of small cell lung cancer in particular. These various compounds act by inhibiting the catalytic activity of topoisomerase II by stabilization of the cleavable complex.

Various modifications have been carried out on these derivatives, such as those described in the patent applications JP 948782, WO 97/13776 and U.S. Pat. No. 3,634,459. Nevertheless, the need for cancer therapies requires the continuous development of new anti-tumor and cytotoxic agents, with the goal of obtaining drugs that are at the same time more active, more soluble and better tolerated.

The compounds of the present invention, in addition to the fact that they are novel, present surprising in vivo and in vitro activity that is higher than that observed to date. Thus, the compounds of the present invention possess properties which make them particularly useful for the treatment of cancers. Among the types of cancers which can be treated by the compounds of the present invention, carcinomas and adenocarcinomas, sarcomas, gliomas and leukemias can be cited on a purely nonrestrictive basis.

More particularly, the present invention relates to the compounds of the formula (I):

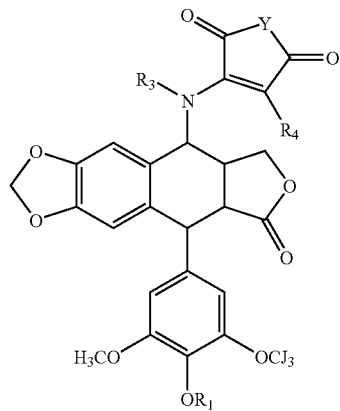

wherein:

$R_1$ represents a group chosen among hydrogen, straight or branched $(C_1-C_6)$alkyl, aryl, straight or branched $(C_1-C_6)$arylalkyl, heteroaryl, straight or branched $(C_1-C_6)$heteroarylalkyl, straight or branched $(C_1-C_6)$alkylcarbonyl, arylcarbonyl, straight or branched $(C_1-C_6)$arylalkylcarbonyl, straight or branched $(C_1-C_6)$alkoxycarbonyl, aryloxycarbonyl, straight or branched $(C_1-C_6)$arylalkoxycarbonyl, heterocycloalkoxycarbonyl, straight or branched $(C_1-C_6)$alkylsulfonyl, arylsulfonyl, straight or branched $(C_1-C_6)$arylalkylsulfonyl, phosphonic, or $Si(R_a)_2R_b$ wherein $R_a$ and $R_b$, identical or different, each represent a group chosen among straight or branched $(C_1-C_6)$alkyl, or aryl, Y represents a group chosen among HN—NH or N—$R_2$ wherein:

$R_2$ represents a group chosen among hydrogen, straight or branched $(C_1-C_6)$alkyl, aryl, heteroaryl, cycloalkyl, heterocycloalkyl, straight or branched $(C_2-C_6)$alkenyl, straight or branched $(C_2-C_6)$alkynyl, or a group of the formula -$T_1$-$R_5$ wherein:

$T_1$ represents a group chosen among a straight or branched $(C_1-C_6)$alkylene chain, optionally substituted by one or more groups chosen among hydroxy or straight or branched $(C_1-C_6)$alkoxy, a straight or branched $(C_2-C_6)$ alkenylene chain, or a straight or branched $(C_2-C_6)$alkynylene chain, $R_5$ represents a group chosen among hydroxy, straight or branched $(C_1-C_6)$alkoxy, straight or branched $(C_1-C_6)$alkylcarbonyl, straight or branched $(C_1-C_6)$alkylcarbonyloxy, straight or branched $(C_1-C_6)$alkoxycarbonyl, carboxy, halogen, trihalogenomethyl, aryl, heteroaryl, cycloalkyl, heterocycloalkyl, $NR_cR_d$ wherein $R_c$, and $R_d$, identical or different, each represent a group chosen among hydrogen, straight or branched $(C_1-C_6)$alkyl, straight or branched $(C_1-C_6)$aminoalkyl, wherein the amino part is optionally substituted by one or two identical or different groups, straight or branched $(C_1-C_6)$alkyl, straight or branched $(C_1-C_6)$hydroxyalkyl, straight or branched $(C_1-C_6)$alkoxy$(C_1-C_6)$alkyl, or $C(O)NR'_cR'_d$ wherein $R'_c$ and $R'_d$, identical or different, each represent a group chosen among hydrogen, straight or branched $(C_1-C_6)$alkyl, straight or branched $(C_1-C_6)$aminoalkyl, wherein the amino part is optionally substituted by one or two identical or different groups, straight or branched $(C_1-C_6)$alkyl, straight or branched $(C_1-C_6)$hydroxyalkyl, straight or branched $(C_1-C_6)$alkoxy$(C_1-C_6)$alkyl, or $R'_c$ and $R'_d$ together form a heterocycloalkyl with the nitrogen atom which carry them, $R_3$ represents a group chosen among hydrogen, straight or branched $(C_1-C_6)$alkyl, cycloalkyl, straight or branched $(C_1-C_6)$cycloalkylalkyl, aryl, or straight or branched $(C_1-C_6)$arylalkyl, $R_4$ represents a group chosen among hydrogen, straight or branched $(C_1-C_6)$alkyl, the enantiomers, diastereoisomers, and addition salts thereof to a pharmaceutically acceptable acid or base, it being understood that:

by aryl is meant a group chosen among phenyl, biphenyl, naphthyl, dihydronaphthyl, tetrahydronaphthyl, indenyl, indanyl, and benzocyclobutyl, each of these groups optionally containing one or more substitutions, identical or different, chosen among halogen, hydroxy, straight or branched $(C_1-C_6)$alkyl, straight or branched $(C_1-C_6)$alkoxy, cyano, nitro, amino, straight or branched $(C_1-C_6)$alkylamino, straight or branched $(C_1-C_6)$dialkylamino, carboxy, straight or branched $(C_1-C_6)$ alkoxycarbonyl, straight or branched ($C_1$-$C_6$)trihalogenoalkyl, straight or branched ($C_1$-$C_6$)alkylcarbonyloxy, straight or branched ($C_1$-$C_6$)alkylcarbonyl, and aminocarbonyl wherein the amino part is optionally substituted by one or two groups, identical or different, straight or branched ($C_1$-$C_6$)alkyl, by heteroaryl is meant a monocyclic or bicyclic aromatic group or a bicyclic group of which one of the rings is aromatic and the other ring is partially hydrogenated, from 5 to 12 links, containing within the cyclic system from one to three heteroatoms, identical or different, selected among oxygen, nitrogen and sulfur, the aforementioned heteroaryl group being optionally substituted by one or more identical or different groups, selected among the substituents defined previously in the case of the aryl group; among the heteroaryl groups, pyridyl, pyrrolyl, thienyl, furyl, pyrazinyl, isothiazolyl, thiazolyl, oxazolyl, isoxazolyl, pyrimidinyl, indolyl, benzofuranyl, benzothienyl, quinolyl, isoquinolyl, benzo[1,4]dioxynyl and 2,3-dihydrobenzo[1,4]dioxynyl can be cited on a purely nonrestrictive basis, by cycloalkyl is meant a monocyclic or bicyclic group, saturated or unsaturated but without an aromatic character, containing from 3 to 12 carbon atoms, being optionally substituted by one or more groups, identical or different, selected among halogen, straight or branched ($C_1$-$C_6$)alkyl, straight or branched ($C_1$-$C_6$)trihalogenoalkyl, hydroxy, amino, straight or branched ($C_1$-$C_6$)alkylamino, and straight or branched ($C_1$-$C_6$)dialkylamino; among the cycloalkyl groups, cyclopropyl, cyclobutyl, cyclopentyl, and cyclohexyl can be cited on a purely nonrestrictive basis, by heterocycloalkyl is meant a cycloalkyl such as defined previously, containing within the cyclic system, from one to two heteroatoms, identical or different, selected among oxygen and nitrogen, the aforementioned heterocycloalkyl being optionally substituted by one or more identical or different groups defined previously in the case of the cycloalkyl group; among the heterocycloalkyl groups, piperidyl, piperazinyl, morpholyl can be cited on a purely nonrestrictive basis.

Among the pharmaceutically acceptable acids, hydrochloric, hydrobromic, sulfuric, phosphoric, acetic, trifluoroacetic, lactic, pyruvic, malonic, succinic, glutaric, fumaric, tartaric, maleic, citric, ascorbic, oxalic, methane sulphonic and camphoric acids, etc., can be cited on a nonrestrictive basis.

Among the pharmaceutically acceptable bases, sodium hydroxide, potassium hydroxide, triethylamine, tert-butylamine, etc., can be cited on a nonrestrictive basis.

The preferred substituent $R_1$ according to the invention is the hydrogen atom.

The preferred substituent $R_3$ according to the invention is the hydrogen atom.

The preferred substituent $R_4$ according to the invention is the hydrogen atom or the methyl group.

Very advantageously, the preferred compounds of the invention are the compounds of the formula (I) wherein Y represents a HN—NH or N—$R_2$ group wherein $R_2$ represents a straight or branched ($C_1$-$C_6$)alkyl group, straight or branched ($C_2$-$C_6$)alkenyl group, or a group of the formula -$T_1$-$R_5$ wherein $T_1$ and $R_5$ are such as defined in the formula (I).

In a particularly advantageous way, the preferred group Y according to the invention is the group of the formula $NR_2$ wherein $R_2$ represents a methyl group.

Interestingly, the preferred group Y according to the invention is the group of the formula $NR_2$ wherein $R_2$ represents a -$T_1$-$R_5$ group wherein $T_1$ represents a straight or branched ($C_1$-$C_6$)alkylene chain, and $R_5$ represents a group chosen among aryl, carboxy and straight or branched ($C_1$-$C_6$)alkylcarbonyloxy.

More interestingly, the preferred group Y according to the invention is the group of the formula $NR_2$ wherein $R_2$ represents a -$T_1$-$R_5$ group wherein $T_1$ represents a methylene —$CH_2$— group and $R_5$ represents an aryl group.

The preferred compounds of the invention are:

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-methyl-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-benzyl-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(4-(fluorobenzyl)-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[4-(trifluoromethyl)benzyl]-1H-pyrrole-2,5-dione;

N-{4-[(3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-2,5-dioxo-2,5-dihydro-1H-pyrrol-1-yl)methyl]phenyl}acetamide;

6-(3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-2,5-dioxo-2,5-dihydro-1H-pyrrol-1-yl)hexanoic acid;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-butyl-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-allyl-1H-pyrrole-2,5-dione;

2-(3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-2,5-dioxo-2,5-dihydro-1H-pyrrol-1-yl)ethyl acetate;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(2,3-dihydroxypropyl)-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[2-(dimethylamino)ethyl]-1H-pyrrole-2,5-dione;

The enantiomers, diastereoisomers and addition salts to a pharmaceutically acceptable acid or base of the preferred compounds of the invention form an integral part of the invention.

The present invention also extends to the method of preparation of compounds of the formula (I), wherein is used as a starting product a compound of the formula (II):

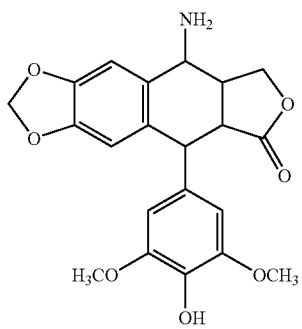

(II)

which is subjected, under basic conditions:
either to the action of a compound of the formula (III):

R'₁-X   (III)

wherein R'₁ represents a group chosen among straight or branched (C₁-C₆)alkyl, aryl, straight or branched (C₁-C₆)arylalkyl, heteroaryl, straight or branched (C₁-C₆)heteroarylalkyl, straight or branched (C₁-C₆)alkylcarbonyl, arylcarbonyl, straight or branched (C₁-C₆)arylalkylcarbonyl, straight or branched (C₁-C₆)alkoxycarbonyl, aryloxycarbonyl, straight or branched (C₁-C₆)arylalkoxycarbonyl, heterocycloalkoxycarbonyl, straight or branched (C₁-C₆)alkylsulfonyl, arylsulfonyl, straight or branched (C₁-C₆)arylalkylsulfonyl, phosphonic, or Si(Rₐ)₂R_b wherein Rₐ and R_b, identical or different, each represent a group chosen among straight or branched (C₁-C₆)alkyl, or aryl, and X represents a hydrogen atom, a halogen atom or an ordinary leaving group of organic chemistry, to lead to the compounds of the formula (IV/a):

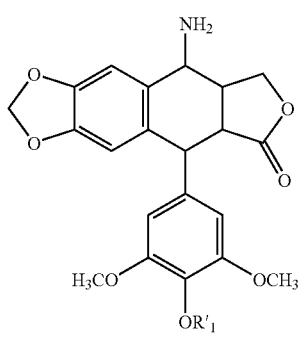

(IV/a)

wherein R'₁ is such as defined previously,
or to the action of a compound of the formula (V):

G-L   (V)

wherein G represents a traditional protective group of hydroxy functions and L an ordinary leaving group of organic chemistry, to lead to the compounds of the formula (IV/b):

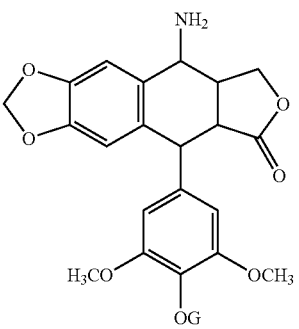

(IV/b)

wherein G is such as defined previously,
the whole of the compounds of the formula (IV/a) and (IV/b) forming the compounds of the formula (IV):

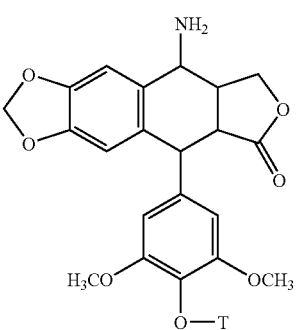

(IV)

wherein T represents an R'₁ group or G such as previously defined, a compound of the formula (IV), which is subjected, under basic conditions, to the action of a compound of the formula (VI):

R'₃—X'   (VI)

wherein R₁₃ represents a group chosen among straight or branched (C₁-C₆)alkyl, cycloalkyl, straight or branched (C₁-C₆)cycloalkylalkyl, aryl or straight or branched (C₁-C₆)arylalkyl, and X' represents a hydrogen atom, a halogen atom or an ordinary leaving group of organic chemistry, to lead to the compounds of the formula (VII):

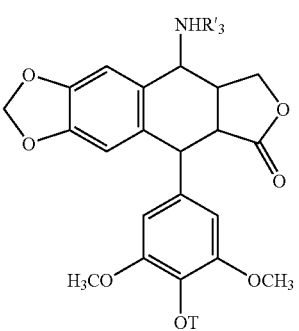

(VII)

wherein R'₃ and T are such as previously defined, the whole of the compounds of the formulas (IV) and (VII) forming the compounds of the formula (VIII):

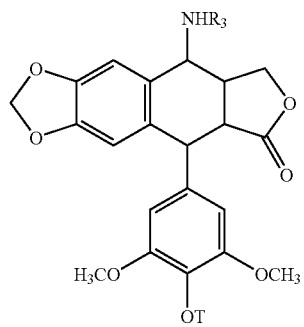
(VIII)

wherein R₃ and T are such as defined in the formula (I)

a compound of the formula (VIII) which are treated in a basic medium by a compound of the formula (IX):

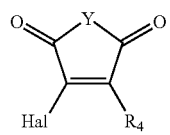
(IX)

wherein Y and R₄ are such as defined in the formula (I), and Hal represents a halogen atom, to lead to the compounds of the formulas (I/a) and (I/b), specific cases of the compounds of the formula (I), according to whether T represents an R₁₁ group or G, respectively:

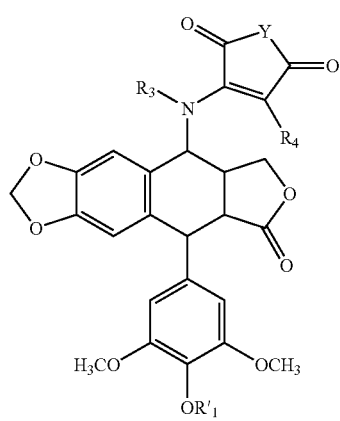
(I/a)

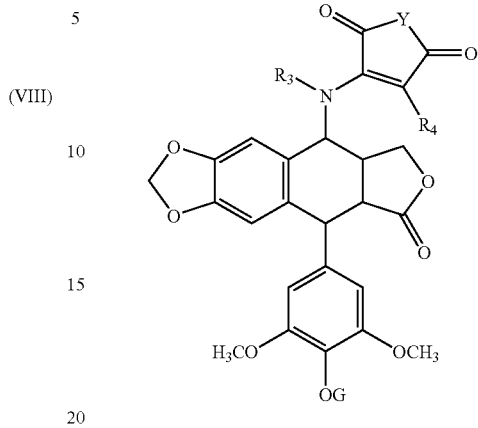
(I/b)

wherein R'₁, R₃, R₄, Y and G are such as previously defined, a compound of the formula (I/b) wherein the hydroxy function is deprotected according to the traditional methods of organic chemistry, to lead to the compounds of the formula (I/c), specific cases of the compounds of the formula (I):

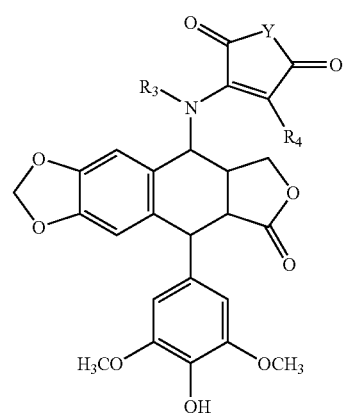
(I/c)

wherein R₃, R₄ and Y are such as previously defined, the compounds (I/a) to (I/c) form the whole of the compounds of the invention, which can be purified, if necessary, according to a traditional purification technique, which can, if it is desired, be separated into the various optical isomers thereof according to a traditional separation technique, and which can be transformed, if it is desired, into the addition salts thereof to a pharmaceutically acceptable acid or base.

The compounds of the formula (II), (III), (V), (VI) and (IX) are either commercial compounds, or are obtained according to the traditional methods of organic synthesis.

The compounds of the formula (I) present particularly interesting anti-tumor properties. They have an excellent in vitro cytotoxicity on cellular lines, arising from murine and human tumors, and are active in vivo. The characteristic properties of these compounds allow their therapeutic use as anti-tumor agents.

The present invention also has as an object the pharmaceutical compositions containing as an active ingredient at least one compound of the formula (I), its optical isomers, or one of its addition salts to a pharmaceutically acceptable acid or base, alone or in combination with one or more nontoxic, pharmaceutically acceptable inert excipients or vehicles.

More particularly cited among the compositions according to the invention are those which are appropriate for administration by oral, parenteral (intravenous, intramuscular or subcutaneous), per- or trans-cutaneous, nasal, rectal, perlingual, ocular or respiratory route, and in particular plain or coated tablets, sublingual tablets, gelatin capsules, capsules, suppositories, creams, pomades, dermal gels, injectable or drinkable preparations, aerosols, ocular or nasal drops, etc.

The useful dosage varies according to the age and the weight of the patient, the administration route, the nature and the severity of the ailment and any associated treatments, and ranges from 0.5 mg to 500 mg in one or more doses per day.

The following examples illustrate the invention but do not limit it in any way. The starting products used are products that are known or are prepared according to known procedures.

PREPARATION 1

(5R,5aR,8aS,9S)-9-amino-5-(4-{[tert-butyl(dimethyl)silyl]oxy}-3,5-dimethoxyphenyl)-5,8,8a,9-tetrahydrofuro[3',4':6,7]naphtho[2,3-d][1,3]dioxol-6(5aH)-one A 63.4 mmol solution of (5R,5aR,8aS,9S)-9-amino-5-(4-hydroxy-3,5-dimethoxyphenyl)-5,8,8a,9-tetrahydrofuro[3',4':6,7]naphtho[2,3-d][1,3]dioxol-6(5aH)-one, 111.8 mmol of tert-butyldimethylsilyl chloride and 510 mmol of imidazole in 1.6 l of anhydrous dimethylformamide is stirred for 20 hours at ambient temperature. The reaction mixture is then washed with 2 l of water then 1 l of ether. The ether phase is then decanted and the aqueous phase extracted with ether. The organic phases are then dried on magnesium sulfate, are filtered and concentrated under reduced pressure. The expected product is obtained by recrystallization in a benzene/heptane mixture.

Melting point: 236-238° C. Mass spectrometry (IC/NH$_3$): m/z=514 [M+H]$^+$, 531 [M+NH$_4$]$^+$

PREPARATION 2

3-Bromo-1-methyl-1H-pyrrole-2,5-dione

A 15 mmol solution of 3-bromo-2,5-furanedione and 15 mmol of methylamine at 40% in water, in 300 ml of glacial acetic acid is carried under reflux for 16 hours. After having allowed the reaction mixture to return to ambient temperature, 20 ml of acetic anhydride are added. The reaction medium is again brought to reflux under stirring for 4 hours before evaporating the solvents under reduced pressure. The expected product is obtained after purification by silica gel chromatography (heptane/ethyl acetate: 1/1) and recrystallization in ethanol.

Melting point: 88-89° C. Mass spectrometry (IC/NH$_3$): m/z=207.209 [M+NH$_4$]$^+$

PREPARATION 3

3-Bromo-1-benzyl-1H-pyrrole-2,5-dione

To a solution of 87.3 mmol of benzylamine in 345 ml of glacial acetic acid are added 87.3 mmol of 3-bromo-2,5-furanedione. The whole is carried under reflux for 16 hours under an argon atmosphere. The reaction mixture is evaporated under reduced pressure after the return to ambient temperature. The residue obtained is taken up with 310 ml of acetic acid to which 62.3 mmol of sodium acetate are added. The whole is again brought under reflux for 2 hours. After the return to ambient temperature, the reaction mixture is washed with 1 l of water and 500 ml of ether. The aqueous phase is then extracted with ether. The organic phases are washed with a saturated solution of sodium chloride (2×300 ml), water (2×500 ml), dried on magnesium sulfate, filtered and concentrated under reduced pressure. A silica gel chromatography (dichloromethane) makes it possible to insolate the expected product.

Mass spectrometry (IC/NH$_3$): m/z=283,29 [M+NH$_4$]$^+$

PREPARATION 4

3-Bromo-1-(4-fluorobenzyl)-1H-pyrrole-2,5-dione

This product is obtained according to the method of the preparation 3 by using 4-fluorobenzylamine in the place of benzylamine.

PREPARATION 5

3-Bromo-1-[(4-trifluoromethyl)benzyl]-1H-pyrrole-2,5-dione

This product is obtained according to the method of the preparation 3 by using 4-trifluoromethylbenzylamine in the place of benzylamine.

PREPARATION 6

3-Bromo-1-[(4-acetamido)benzyl]-1H-pyrrole-2,5-dione

This product is obtained according to the method of the preparation 3 by using 4-acetamidobenzylamine in the place of benzylamine.

PREPARATION 7

3-Bromo-1-[2-hydroxy-1-(hydroxymethyl)ethyl-1H-pyrrole-2,5-dione

This product is obtained according to the method of the preparation 3 by using 2-amino-1,3-propanediol in the place of benzylamine.

PREPARATION 8

(3-Bromo-2,5-dioxo-2,5-dihydro-1H-pyrrol-1-yl)acetic acid

This product is obtained according to the method of the preparation 3 by using glycine in the place of benzylamine.

Melting point: 153-155° C. Mass spectrometry (IC/NH$_3$): m/z=251.25 [M+NH$_4$]$^+$

PREPARATION 9

(3-Bromo-2,5-dioxo-2,5-dihydro-1H-pyrrol-1-yl)-methyl acetate

This product is obtained according to the method of the preparation 3 by using glycine methyl ester in the place of benzylamine.

PREPARATION 10

6-(3-Bromo-2,5-dioxo-2,5-dihydro-1H-pyrrol-1-yl) hexanoic acid

This product is obtained according to the method of the preparation 3 by using 6-aminohexanoic acid in the place of benzylamine.

Melting point: 98-100° C. Mass spectrometry (IC/NH$_3$): m/z=307.31 [M+NH$_4$]$^+$

PREPARATION 11

3-Bromo-1-butyl-1H-pyrrole-2,5-dione

This product is obtained according to the method of the preparation 3 by using butylamine in the place of benzylamine.

Mass spectrometry (IC/NH$_3$): m/z=249.25 [M+NH$_4$]$^+$

PREPARATION 12

(5R,5aR,8aS,9S)-9-Amino-5-(3,4,5-trimethoxyphenyl)-5,8,8a,9-tetrahydrofuro[3',4':6,7]naphtho[2,3-d][1,3]dioxol-6(5aH)-one This product is obtained according to the method of the preparation 1 by using iodomethane in the place of tert-butyldimethylsilyl chloride.

PREPARATION 13

3-Bromo-1,4-dimethyl-1H-pyrrole-2,5-dione

This product is obtained according to the method of the preparation 2 by using 3-bromo-4-methyl-2,5-furanedione in the place of 3-bromo-2,5-furanedione.

PREPARATION 14

(5R,5aR,8aS,9S)-5-(4-{[tert-Butyl(dimethyl)silyl]oxy}-3,5-dimethoxyphenyl)-9-(methylamino)-5,8,8a,9-tetrahydrofuro[3',4':6,7]naphtho[2,3-d][1,3]dioxol-6(5aH)-one This product is obtained according to the method of the example 1 by using iodomethane in the place of the compound of the preparation 2.

PREPARATION 15

3-Bromo-1-(2-hydroxyethyl)-1H-pyrrole-2,5-dione

This product is obtained according to the method of the preparation 3 by using ethanolamine in the place of benzylamine.

PREPARATION 16

3-Bromo-1-(2-methoxyethyl)-1H-pyrrole-2,5-dione

This product is obtained according to the method of the preparation 3 by using 2-methoxyethylamine in the place of benzylamine.

PREPARATION 17

1-Allyl-3-bromo-1H-pyrrole-2,5-dione

This product is obtained according to the method of the preparation 3 by using allylamine in the place of benzylamine.

PREPARATION 18

3-Bromo-1-[2-(1-piperidinyl)ethyl]-1H-pyrrole-2,5-dione

This product is obtained according to the method of the preparation 3 by using 2-(1-piperidinyl)ethylamine in the place of benzylamine.

PREPARATION 19

3-Bromo-1-[2-(4-morpholinyl)ethyl]-1H-pyrrole-2,5-dione

This product is obtained according to the method of the preparation 3 by using 2-(4-morpholinyl)ethylamine in the place of benzylamine.

PREPARATION 20

4-Bromo-1,2-dihydro-3,6-pyridazinedione

This product is obtained according to the method of the preparation 3 by using hydrazine hydrate in the place of benzylamine.

Melting point: 274-276° C. Mass spectrometry (IC/NH$_3$): m/z=208.21 [M+NH$_4$]$^+$

PREPARATION 21

2-(3-Bromo-2,5-dioxo-2,5-dihydro-1H-pyrrol-1-yl) ethyl acetate

This product is obtained according to the method of the preparation 3 by using 2-aminoethyl acetate in the place of benzylamine.

PREPARATION 22

7-(3-Bromo-2,5-dioxo-2,5-dihydro-1H-pyrrol-1-yl) heptanoic acid

This product is obtained according to the method of the preparation 3 by using 7-aminohexanoic acid in the place of benzylamine.

PREPARATION 23

3-Bromo-1-(2,3-dihydroxypropyl)-1H-pyrrole-2,5-dione

This product is obtained according to the method of the preparation 3 by using 3-amino-1,2-propanediol in the place of benzylamine.

PREPARATION 24

3-Bromo-1-[2-(4-methyl-1-piperazinyl)ethyl]-1H-pyrrole-2,5-dione

This product is obtained according to the method of the preparation 3 by using 2-(4-methyl-1-piperazinyl)ethylamine in the place of benzylamine.

PREPARATION 25

3-Bromo-1-[2-(dimethylamino)ethyl-1H-pyrrole-2,5-dione

This product is obtained according to the method of the preparation 3 by using N-(2-aminoethyl)-N,N-dimethylamine in the place of benzylamine.

PREPARATION 26

3-Bromo-1-[2-(butylamino)ethyl]-1H-pyrrole-2,5-dione

This product is obtained according to the method of the preparation 3 by using N-(2-aminoethyl)-N-butylamine in the place of benzylamine.

PREPARATION 27

3-Bromo-1-[2-{[2-(dimethylamino)ethyl]amino}ethyl)-1H-pyrrole-2,5-dione

This product is obtained according to the method of the preparation 3 by using N-(2-aminoethyl)-N-[2-(dimethylamino)ethyl]amine in the place of benzylamine.

EXAMPLE 1

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',41:6,7]naphtho[2,3-d][1,3]dioxol-5-yl]amino}-1-methyl-1H-pyrrole-2,5-dione To a 4 mmol solution of the compound of the preparation 2 and of 3.6 mmol of the compound of the preparation 1 in 50 ml of anhydrous dimethylformamide under inert atmosphere are added 4.4 mmol of triethylamine. The reaction mixture is stirred at ambient temperature for 24 hours. The solvent is evaporated under reduced pressure and the residue is taken up in a mixture of water (120 ml) and dichloromethane (200 ml). The aqueous phase is extracted with dichloromethane (3×40 ml). The organic phases are dried on magnesium sulfate, filtered and evaporated under reduced pressure. A silica gel chromatography (dichloromethane/acetone:95/5) makes it possible to isolate the expected product.

Mass spectrometry (IC/NH$_3$): m/z=640 [M+NH$_4$]$^+$

EXAMPLE 2

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-methyl-1H-pyrrole-2,5-dione To a solution of 1.34 mmol of the compound of the example 1 dissolved in 125 ml of methanol are added 8 g of Dowex resin (50×2-200) rinsed beforehand with water then methanol. The reaction mixture is stirred for 18 hours, then filtered and rinsed with acetone. The solvents are evaporated under reduced pressure. The expected product is obtained after purification by silica gel chromatography (dichloromethane/acetone: 9/1) and recrystallization in a benzene/heptane mixture.

Melting point: 238-241° C. Mass spectrometry (IC/NH$_3$): m/z=526 [M+NH$_4$]$^+$

EXAMPLE 3

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-benzyl-1H-pyrrole-2,5-dione This product is obtained according to the method of the example 1 by using compound of the preparation 3 in the place of the compound of the preparation 2. Mass spectrometry (IC/NH$_3$): m/z=715 [M+NH$_4$]$^+$

EXAMPLE 4

3-{[(5S,5aS,8aR,9R)-9-(4-Hydroxo-3,5-dimethoxyphenyl)-8-oxo-5,5a,6,8,8a,9-hexahydrofuro[3',4':6,7]naphtho[2,3-d][1,3]dioxol-5-yl]amino}-1-benzyl-1H-pyrrole-2,5-dione This product is obtained according to the method of the example 2 by using the compound of the example 3.

Melting point: 220-223° C. Mass spectrometry (IC/NH$_3$): m/z=602 [M+NH$_4$]$^+$

EXAMPLE 5

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-(4-fluorobenzyl)-1H-pyrrole-2,5-dione This product is obtained according to the method of the example 1 by using the compound of the preparation 4 in the place of the compound of the preparation 2.

Melting point: 182-184° C. Mass spectrometry (IC/NH$_3$): m/z=734 [M+NH$_4$]$^+$

EXAMPLE 6

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(4-fluorobenzyl)-1H-pyrrole-2,5-dione This product is obtained according to the method of the example 2 by using the compound of the example 5.

Melting point: 214-216° C. Mass spectrometry (IC/NH$_3$): m/z=620 [M+NH$_4$]$^+$

EXAMPLE 7

3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',41:6,7]naphtho[2,3-d][1,3]dioxol-5-yl]amino}-1-[4-(trifluoromethyl)benzyl]-1H-pyrrole-2,5-dione This product is obtained according to the method of the example 1 by using the compound of the preparation 5 in the place of the compound of the preparation 2.

Melting point: 180-182° C. Mass spectrometry (IC/NH$_3$): m/z=784 [M+NH$_4$]$^+$

EXAMPLE 8

3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-1-[4-(trifluoromethyl)benzyl]-1H-pyrrole-2,5-dione This product is obtained according to the method of the example 2 by using the compound of the example 7.

Melting point: 184-186° C. Mass spectrometry (IC/NH$_3$): m/z=670 [M+NH$_4$]$^+$

EXAMPLE 9

N-{4-[(3-{[(5S,5aS,8aR,9R)-9-(4-{[tert-Butyl(dimethyl)silyl]oxy}-3,5-dimethoxyphenyl)-8-oxo-5,5a,6, 8,8a,9-hexahydrofuro[3',4':6,7]naphtho[2,3-d][1,3] dioxol-5-yl]amino}-2,5-dioxo-2,5-dihydro-1H-pyrrol-1-yl)methyl]phenyl}-acetamide This product is obtained according to the method of the example 1 by using the compound of the preparation 6 in the place of the compound of the preparation 2.

Melting point: 177-179° C. Mass spectrometry (IC/NH$_3$): m/z=773 [M+NH$_4$]$^+$

EXAMPLE 10

N-{4-[(3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl] amino}-2,5-dioxo-2,5-dihydro-1H-pyrrol-1-yl) methyl]phenyl}-acetamide This product is obtained according to the method of the example 2 by using the compound of the example 9.

Melting point: 200-204° C. (decomposition) Mass spectrometry (IC/NH$_3$): m/z=659 [M+NH$_4$]$^+$

EXAMPLE 11

3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-1-[2-hydroxy-1-(hydroxymethyl)ethyl]-1H-pyrrole-2,5-dione This product is obtained according to the method of the example 1 by using the compound of the preparation 7 in the place of the compound of the preparation 2.

EXAMPLE 12

3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-1-[2-hydroxy-1-(hydroxymethyl)ethyl]-1H-pyrrole-2,5-dione This product is obtained according to the method of the example 2 by using the compound of the example 11.

EXAMPLE 13

(3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-2,5-dioxo-2,5-dihydro-1H-pyrrol-1-yl) acetic acid This product is obtained according to the method of the example 1 by using the compound of the preparation 8 in the place of the compound of the preparation 2.

EXAMPLE 14

(3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-2,5-dioxo-2,5-dihydro-1H-pyrrol-1-yl) acetic acid This product is obtained according to the method of the example 2 by using the compound of the example 13.

EXAMPLE 15

3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-2,5-dioxo-2,5-dihydro-1H-pyrrol-1-yl) methyl acetate This product is obtained according to the method of the example 1 by using the compound of the preparation 9 in the place of the compound of the preparation 2.

EXAMPLE 16

3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-2,5-dioxo-2,5-dihydro-1H-pyrrol-1-yl)methyl acetate This product is obtained according to the method of the example 2 by using the compound of the example 15.

EXAMPLE 17

6-(3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-2,5-dioxo-2,5-dihydro-1H-pyrrol-1-yl) hexanoic acid This product is obtained according to the method of the example 1 by using the compound of the preparation 10 in the place of the compound of the preparation 2.

EXAMPLE 18

6-(3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-2,5-dioxo-2,5-dihydro-1H-pyrrol-1-yl) hexanoic acid This product is obtained according to the method of the example 2 by using the compound of the example 17.
Melting point: 150-152° C. Mass spectrometry (IC/NH$_3$): m/z=626 [M+NH$_4$]$^+$

EXAMPLE 19

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',41:6,7]naphtho[2,3-d][1,3]dioxol-5-yl]amino}-1-butyl-1H-pyrrole-2,5-dione This product is obtained according to the method of the example 1 by using the compound of the preparation 11 in the place of the compound of the preparation 2.

EXAMPLE 20

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-butyl-1H-pyrrole-2,5-dione This product is obtained according to the method of the example 2 by using the compound of the example 19.
Mass spectrometry (IC/NH$_3$): m/z=568 [M+NH$_4$]$^+$

EXAMPLE 21

3-{[(5S,5aS,8aR,9R)-8-Oxo-9-(3,4,5-trimethoxyphenyl)-5,5a,6,8,8a,9-hexahydrofuro[3',4':6,7]naphtho[2,3-d][1,3]dioxol-5-yl]amino}-1-methyl-1H-pyrrole-2,5-dione This product is obtained according to the method of the example 1 by using the compound of the preparation 12 in the place of the compound of the preparation 1.

EXAMPLE 22

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1,4-dimethyl-1H-pyrrole-2,5-dione This product is obtained according to the method of the example 1 by using the compound of the preparation 13 in the place of the compound of the preparation 2.

EXAMPLE 23

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1,4-dimethyl-1H-pyrrole-2,5-dione This product is obtained according to the method of the example 2 by using the compound of the example 22.

Melting point: 172-176° C. Mass spectrometry (IC/NH$_3$): m/z=540 [M+NH$_4$]$^+$

EXAMPLE 24

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl](methyl)amino}-1-methyl-1H-pyrrole-2,5-dione This product is obtained according to the method of the example 1 by using the compound of the preparation 14 in the place of the compound of the preparation 1.

EXAMPLE 25

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl](methyl)amino}-1-methyl-1H-pyrrole-2,5-dione This product is obtained according to the method of the example 2 by using the compound of the example 24.

EXAMPLE 26

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-(2-hydroxyethyl)-1H-pyrrole-2,5-dione This product is obtained according to the method of the example 1 by using the compound of the preparation 15 in the place of the compound of the preparation 2.

EXAMPLE 27

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(2-hydroxyethyl)-1H-pyrrole-2,5-dione This product is obtained according to the method of the example 2 by using the compound of the example 26.

EXAMPLE 28

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-(2-methoxyethyl)-1H-pyrrole-2,5-dione This product is obtained according to the method of the example 1 by using the compound of the preparation 16 in the place of the compound of the preparation 2.

EXAMPLE 29

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(2-methoxyethyl)-1H-pyrrole-2,5-dione This product is obtained according to the method of the example 2 by using the compound of the example 28.

EXAMPLE 30

3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-1-allyl-1H-pyrrole-2,5-dione This product is obtained according to the method of the example 1 by using the compound of the preparation 17 in the place of the compound of the preparation 2.

EXAMPLE 31

3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-1-allyl-1H-pyrrole-2,5-dione This product is obtained according to the method of the example 2 by using the compound of the example 30.
Melting point: 180-183° C. Mass spectrometry (IC/NH$_3$): m/z=552 [M+NH$_4$]$^+$

EXAMPLE 32

3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-1-[2-(1-piperidinyl)ethyl]-1H-pyrrole-2,5-dione This product is obtained according to the method of the example 1 by using the compound of the preparation 18 in the place of the compound of the preparation 2.

EXAMPLE 33

3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-1-[2-(1-piperidinyl)ethyl]-1H-pyrrole-2,5-dione This product is obtained according to the method of the example 2 by using the compound of the example 32.

EXAMPLE 34

3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-1-[2-(4-morpholinyl)ethyl]-1H-pyrrole-2,5-dione This product is obtained according to the method of the example 1 by using the compound of the preparation 19 in the place of the compound of the preparation 2.

EXAMPLE 35

3-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-1-[2-(4-morpholinyl)ethyl]-1H-pyrrole-2,5-dione This product is obtained according to the method of the example 2 by using the compound of the example 34.

EXAMPLE 36

4-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-1,2-dihydro-3,6-pyridazinedione This product is obtained according to the method of the example 1 by using the compound of the preparation 20 in the place of the compound of the preparation 2.

EXAMPLE 37

4-{[(5S,5aS,8aR,9R)-9-(4-Hydroxy-3,5-dimethoxyphenyl)-8-oxo-5,5a,6,8,8a,9-hexahydrofuro[3',4':6, 7]naphtho[2,3-d][1,3]dioxol-5-yl]amino}-1,2-dihydro-3,6-pyridazinedione This product is obtained according to the method of the example 2 by using the compound of the example 36.

EXAMPLE 38

2-(3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-2,5-dioxo-2,5-dihydro-1H-pyrrol-1-yl) ethyl acetate This product is obtained according to the method of the example 1 by using the compound of the preparation 21 in the place of the compound of the preparation 2.

EXAMPLE 39

2-(3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl] amino}-2,5-dioxo-2,5-dihydro-1H-pyrrol-1-yl)ethyl acetate This product is obtained according to the method of the example 2 by using the compound of the example 38.
Mass spectrometry (IC/NH$_3$): m/z=598 [M+NH$_4$]$^+$

EXAMPLE 40

7-(3-{[(5S,5aS,8aR,9R)-9-(4-{[tert-Butyl(dimethyl) silyl]oxy}-3,5-dimethoxyphenyl)-8-oxo-5,5a,6,8,8a, 9-hexahydrofuro[3',4':6,7]naphtho[2,3-d][1,3]dioxol-5-yl]amino}-2,5-dioxo-2,5-dihydro-1H-pyrrol-1-yl) heptanoic acid This product is obtained according to the method of the example 1 by using the compound of the preparation 22 in the place of the compound of the preparation 2.

EXAMPLE 41

7-(3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl] amino}-2,5-dioxo-2,5-dihydro-1H-pyrrol-1-yl) heptanoic acid This product is obtained according to the method of the example 2 by using the compound of the example 40.

EXAMPLE 42

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-(2,3-dihydroxypropyl)-1H-pyrrole-2,5-dione This product is obtained according to the method of the example 1 by using the compound of the preparation 23 in the place of the compound of the preparation 2.

EXAMPLE 43

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d](1,3]dioxol-5-yl]amino}-1-(2,3-dihydroxypropyl)-1H-pyrrole-2,5-dione This product is obtained according to the method of the example 2 by using the compound of the example 42.

EXAMPLE 44

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-[2-(4-methyl-1-piperazinyl)ethyl]-1H-pyrrole-2,5-dione This product is obtained according to the method of the example 1 by using the compound of the preparation 24 in the place of the compound of the preparation 2.

EXAMPLE 45

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[2-(4-methyl-1-piperazinyl)ethyl]-1H-pyrrole-2,5-dione This product is obtained according to the method of the example 2 by using the compound of the example 44.

EXAMPLE 46

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][11,3]dioxol-5-yl]amino}-1-[2-(dimethylamino)ethyl]-1H-pyrrole-2,5-dione This product is obtained according to the method of the example 1 by using the compound of the preparation 25 in the place of the compound of the preparation 2.

EXAMPLE 47

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[2-(dimethylamino)ethyl]-1H-pyrrole-2,5-dione This product is obtained according to the method of the example 2 by using the compound of the example 46.

EXAMPLE 48

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-[2-(butylamino)ethyl]-1H-pyrrole-2,5-dione This product is obtained according to the method of the example 1 by using the compound of the preparation 26 in the place of the compound of the preparation 2.

EXAMPLE 49

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[2-(butylamino)ethyl]-1H-pyrrole-2,5-dione This product is obtained according to the method of the example 2 by using the compound of the example 48.

EXAMPLE 50

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',41:6,7]naphtho[2,3-d][1,3]dioxol-5-yl]amino}-1-(2-{[2-(dimethylamino)ethyl]amino}ethyl-1H-pyrrole-2,5-dione This product is obtained according to the method of the example 1 by using the compound of the preparation 27 in the place of the compound of the preparation 2.

EXAMPLE 51

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(2-{[2-(dimethylamino)ethyl]amino}ethyl-1H-pyrrole-2,5-dione This product is obtained according to the method of the example 2 by using the compound of the example 50.

EXAMPLE 52

3-{[(5S,5aS,8aR,9R)-9-(4-{[tert-Butyl(dimethyl)silyl]oxy}-3,5-dimethoxyphenyl)-8-oxo-5,5a,6,8,8a,9-hexahydrofuro[3',4':6,7]naphtho[2,3-d][1,3]dioxol-5-yl]amino}-1-[2-(4-methyl-1-piperazinyl)-2-oxoethyl]-1H-pyrrole-2,5-dione This product is obtained by reacting 1-methylpiperazine with the compound of the example 13.

EXAMPLE 53

3-{[(5S,5aS,8aR,9R)-9-(4-Hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[2-(4-methyl-1-piperazinyl)-2-oxoethyl]-1H-pyrrole-2,5-dione This product is obtained according to the method of the example 2 by using the compound of the example 52.

Pharmacological Study of the Compounds of the Invention

EXAMPLE 54

In Vitro Activity

Six cell lines were used:
1 murine leukemia: L1210
1 human epidermal carcinoma: KB-3-1
1 human pulmonary carcinoma, not small cell: A549
1 melanoma: A375
1 neuroblastoma: SK-N-MC
1 fibrosarcoma: HT1080

The cells are cultivated in complete RPMI 1640 culture medium containing 10% of fetal calf serum, 2 mM of glutamine, 50 U/ml of penicillin, 50 μg/ml of streptomycin and 10 mM of Hepes, pH: 7.4. The cells are distributed in microplates and exposed to cytotoxic compounds for 4 doubling times, which is 48 hours. The number of viable cells is then quantified by a calorimetric assay, the microculture tetrazolium assay (J. Carmichael et al., Cancer Res.; 47, 936-942, (1987)). The results are expressed as $IC_{50}$, the cytotoxic concentration that inhibits the proliferation of the treated cells by 50%.

During this test, the compounds of examples 2 and 4 present an $IC_{50}$ on L1210 of 54 nM and 29 nM, respectively.

| Cell lines | $IC_{50}$ (nM) Example 2 |
|---|---|
| L1210 | 54 |
| KB-3-1 | 66.6 |
| A549 | 110 |
| A375 | 44.2 |
| SK-N-MC | 106 |
| HT1080 | 75.8 |

EXAMPLE 55

Action on the Cell Cycle

The L1210 cells are incubated for 21 hours at 37° C. in the presence of various concentrations of the products tested. The cells then are fixed with 70% ethanol (v/v), washed twice in PBS and incubated for 30 minutes at 20° C. in PBS containing 100 μg/ml of RNase and 50 μg/ml of propidium iodide. The results are expressed as a percentage of cells accumulated in phase G2+M after 21 hours compared to the control (control: 20%). The compounds of examples 2 and 4 induce an accumulation of 70% and 81%, respectively, of the cells in phase G2+M after 21 hours at a concentration of 250 nM.

EXAMPLE 56

In Vivo Activity

*Anti-Tumor Activity of the Compounds on P388 Leukemia and on A549 Human Pulmonary Carcinoma:

The P388 line (murine leukemia) was provided by the National Cancer Institute (Frederick, Md., USA). The tumor cells ($10^6$ cells) were inoculated on day 0 in the peritoneal cavity of female BDF1 mice (Iffa-Credo, France) weighing from 18 to 20 g (groups of 6 animals). The products were administered intravenously on day 1.

The anti-tumor activity is expressed in T/C %:

T/C%=(median survival time of the treated animals)/
(median survival time of the control animals)×100

For informational purposes only, the compound of the example 2 is active on P388 leukemia and on A549 human pulmonary carcinoma and it induces a T/C of >575% at 50 mg/kg, with 50% of the animals surviving as of day 60 and a T/C of 225% at 3.12 mg/kg for P388 and A549, respectively.

The invention claimed is:
1. Compounds of the formula (I):

(I)

wherein:
$R_1$ represents a group chosen among hydrogen, straight or branched ($C_1$-$C_6$)alkyl, aryl, straight or branched ($C_1$-$C_6$)arylalkyl, heteroaryl, straight or branched ($C_1$-$C_6$) heteroarylalkyl, straight or branched ($C_1$-$C_6$)alkylcarbonyl, arylcarbonyl, straight or branched ($C_1$-$C_6$) arylalkylcarbonyl, straight or branched ($C_1$-$C_6$) alkoxycarbonyl, aryloxycarbonyl, straight or branched ($C_1$-$C_6$)arylalkoxycarbonyl, heterocycloalkoxycarbonyl, straight or branched ($C_1$-$C_6$)alkylsulfonyl, arylsulfonyl, straight or branched ($C_1$-$C_6$)arylalkylsulfonyl, phosphonic, or Si($R_a$)$_2R_b$ wherein $R_a$ and $R_b$, identical or different, each represent a group chosen among straight or branched ($C_1$-$C_6$)alkyl, or aryl, Y represents a group chosen among HN—NH or N—$R_2$ wherein:

when Y represents NH—NH group, it forms with the rest of the molecule the following 6-membered ring:

when Y represents N—$R_2$ group, it forms with the rest of the molecule the following 5-membered ring:

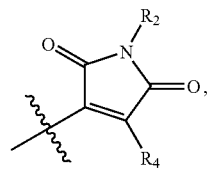

$R_2$ represents a group chosen among hydrogen, straight or branched ($C_1$-$C_6$)alkyl, aryl, heteroaryl, cycloalkyl, heterocycloalkyl, straight or branched ($C_2$-$C_6$)alkenyl, straight or branched ($C_2$-$C_6$)alkynyl, or a group of the formula -$T_1$-$R_5$ wherein:
$T_1$ represents a group chosen among a straight or branched ($C_1$-$C_6$)alkylene chain, optionally substituted by one or more groups chosen among hydroxy or straight or branched ($C_1$-$C_6$)alkoxy, a straight or branched ($C_2$-$C_6$)alkenylene chain, or a straight or branched ($C_2$-$C_6$)alkynylene chain,
$R_5$ represents a group chosen among hydroxy, straight or branched ($C_1$-$C_6$)alkoxy, straight or branched ($C_1$-$C_6$) alkylcarbonyl, straight or branched ($C_1$-$C_6$)alkylcarbonyloxy, straight or branched ($C_1$-$C_6$)alkoxycarbonyl, carboxy, halogen, trihalogenomethyl, aryl, heteroaryl, cycloalkyl, heterocycloalkyl, $NR_cR_d$ wherein $R_c$ and $R_d$, identical or different, each represent a group chosen among hydrogen, straight or branched ($C_1$-$C_6$)alkyl, straight or branched ($C_1$-$C_6$)aminoalkyl, wherein the amino part is optionally substituted by one or two identical or different groups, straight or branched ($C_1$-$C_6$)alkyl, straight or branched ($C_1$-$C_6$)hydroxyalkyl, straight or branched ($C_1$-$C_6$)alkoxy ($C_1$-$C_6$)alkyl, or C(O)$NR'_cR'_d$ wherein $R'_c$ and $R'_d$, identical or different, each represent a group chosen among hydrogen, straight or branched ($C_1$-$C_6$)alkyl, straight or branched ($C_1$-$C_6$)aminoalkyl, wherein the amino part is optionally substituted by one or two identical or different groups, straight or branched ($C_1$-$C_6$)alkyl, straight or branched ($C_1$-$C_6$)hydroxyalkyl, straight or branched ($C_1$-$C_6$)alkoxy ($C_1$-$C_6$)alkyl, or $R'_c$ and $R'_d$ together form a heterocycloalkyl with the nitrogen atom which carry them,
$R_3$ represents a group chosen among hydrogen, straight or branched ($C_1$-$C_6$)alkyl, cycloalkyl, straight or branched ($C_1$-$C_6$)cycloalkylalkyl, aryl, or straight or branched ($C_1$-$C_6$)arylalkyl,
$R_4$ represents a group chosen among hydrogen, straight or branched ($C_1$-$C_6$)alkyl,
the enantiomers, diastereoisomers, and addition salts thereof to a pharmaceutically acceptable acid or base,
it being understood that:
by aryl is meant a group chosen among phenyl, biphenyl, naphthyl, dihydronaphthyl, tetrahydronaphthyl, indenyl, indanyl, and benzocyclobutyl, each of these groups optionally containing one or more substitutions, identical or different, chosen among halogen, hydroxy, straight or branched ($C_1$-$C_6$)alkyl, straight or branched ($C_1$-$C_6$)alkoxy, cyano, nitro, amino, straight or branched ($C_1$-$C_6$)alkylamino, straight or branched ($C_1$-$C_6$)dialkylamino, carboxy, straight or branched ($C_1$-$C_6$)alkoxycarbonyl, straight or branched ($C_1$-$C_6$)trihalogenoalkyl, straight or branched ($C_1$-$C_6$)alkylcarbonyloxy, straight or branched ($C_1$-$C_6$)alkylcarbonyl, and aminocarbonyl wherein the amino part is optionally substituted by one or two groups, identical or different, straight or branched ($C_1$-$C_6$)alkyl, by heteroaryl is meant a monocyclic or bicyclic aromatic group or a bicyclic group of which one of the rings is aromatic and the other ring is partially hydrogenated, from 5 to 12 links, containing within the cyclic system from one to three heteroatoms, identical or different, selected among oxygen, nitrogen and sulfur, the aforementioned heteroaryl group optionally being substituted by one or more identical or different groups, selected among the substituents defined previously in the case of the aryl group;
by cycloalkyl is meant a monocyclic or bicyclic group, saturated or unsaturated but without an aromatic character, containing from 3 to 12 carbon atoms, being optionally substituted by one or more groups, identical or different, selected among halogen, straight or branched ($C_1$-$C_6$)alkyl, straight or branched ($C_1$-$C_6$) trihalogenoalkyl, hydroxy, amino, straight or branched ($C_1$-$C_6$)alkylamino, and straight or branched ($C_1$-$C_6$) dialkylamino;
by heterocycloalkyl is meant a cycloalkyl such as defined previously, containing within the cyclic system, from one to two heteroatoms, identical or different, selected among oxygen and nitrogen, the aforementioned heterocycloalkyl being optionally substituted by one or more identical or different groups defined previously in the case of the cycloalkyl group.

2. Compounds of the formula (I) according to claim 1 wherein $R_1$ represents a hydrogen atom, the enantiomers, diastereoisomers and addition salts thereof to a pharmaceutically acceptable acid or base.

3. Compounds of the formula (I) according to claim 1 wherein $R_3$ represents a hydrogen atom, the enantiomers, diastereoisomers and addition salts thereof to a pharmaceutically acceptable acid or base.

4. Compounds of the formula (I) according to claim 1 wherein $R_4$ represents a hydrogen atom or a methyl group, the enantiomers, diastereoisomers and addition salts thereof to a pharmaceutically acceptable acid or base.

5. Compounds of the formula (I) according to claim 1 wherein Y represents a HN—NH or N—$R_2$ group as defined in claim 1 wherein $R_2$ represents a straight or branched ($C_1$-$C_6$)alkyl group, straight or branched ($C_2$-$C_6$)alkenyl group, or a group of the formula -$T_1$-$R_5$ wherein $T_1$ and $R_5$ are such as defined in the formula (I), the enantiomers, diastereoisomers and addition salts thereof to a pharmaceutically acceptable acid or base.

6. Compounds of the formula (I) according to claim 1 wherein Y represents a group of the formula $NR_2$ as defined in claim 1 wherein $R_2$ represents a methyl group, the enantiomers, diastereoisomers and addition salts thereof to a pharmaceutically acceptable acid or base.

7. Compounds of the formula (I) according to claim 1 wherein Y represents a group of the formula $NR_2$ as defined in claim 1 wherein $R_2$ represents a -$T_1$-$R_5$ group wherein $T_1$ represents a straight or branched ($C_1$-$C_6$)alkylene chain, and $R_5$ represents a group chosen among aryl, carboxy and straight or branched ($C_1$-$C_6$)alkylcarbonyloxy, the enantiomers, diastereoisomers and addition salts thereof to a pharmaceutically acceptable acid or base.

8. Compounds of the formula (I) according to claim 1 wherein Y represents a group of the formula $NR_2$ as defined in claim 1 wherein $R_2$ represents a -$T_1$-$R_5$ group wherein $T_1$ represents a methylene —$CH_2$— group and $R_5$ represents an aryl group, the enantiomers, diastereoisomers and addition salts thereof to a pharmaceutically acceptable acid or base.

9. Compounds of the formula (I) according to claim 1 which are:

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-methyl-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro [3',4'6,7]naphtho [2,3-d][1,3]dioxol-5-yl]amino}-1-benzyl-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(4-(fluorobenzyl)-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[4-(trifluoromethyl)benzyl]-1H-pyrrole-2,5-dione;

N-{4-[(3-{[(5S,5aS,8aR,9R)-9-(4-hydroxy-3,5-dimethoxyphenyl)-8-oxo-5,5a,6,8,8a,9-hexahydrofuro [3',4':6,7]naphtho[2,3-d][1,3]dioxol-5-yl]amino}-2,5-dioxo-2,5-dihydro-1H-pyrrol-1-yl)methyl]phenyl}acetamide;

6-(3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-2,5-dioxo-2,5-dihydro-1H-pyrrol-1-yl) hexanoic acid;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-butyl-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-allyl-1H-pyrrole-2,5-dione;

2-(3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-2,5-dioxo-2,5-dihydro-1H-pyrrol-1-yl) ethyl acetate;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-(2,3-dihydroxypropyl)-1H-pyrrole-2,5-dione;

3-{[(5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl]amino}-1-[2-dimethylamino]ethyl]-1H-pyrrole-2,5-dione.

10. A method for the preparation of the compounds of the formula (I) according to claim 1, wherein is used as starting product a compound of the formula (II):

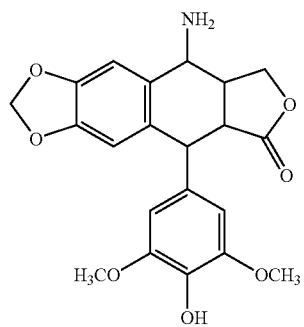

(II)

which is subjected, under basic conditions:
either to the action of a compound of the formula (III):

R'1-X  (III)

wherein R'$_1$ represents a group chosen among straight or branched (C$_1$-C$_6$)alkyl, aryl, straight or branched (C$_1$-C$_6$)arylalkyl, heteroaryl, straight or branched (C$_1$-C$_6$) heteroarylalkyl, straight or branched (C$_1$-C$_6$)alkylcarbonyl, arylcarbonyl, straight or branched (C$_1$-C$_6$) arylalkylcarbonyl, straight or branched (C$_1$-C$_6$) alkoxycarbonyl, aryloxycarbonyl, straight or branched (C$_1$-C$_6$)arylalkoxycarbonyl, heterocycloalkoxycarbonyl, straight or branched (C$_1$-C$_6$)alkylsulfonyl, arylsulfonyl, straight or branched (C$_1$-C$_6$)arylalkylsulfonyl, phosphonic, or Si(R$_a$)$_2$R$_b$ wherein R$_a$ and R$_b$, identical or different, each represent a group chosen among straight or branched (C$_1$-C$_6$)alkyl, or aryl, and X represents a hydrogen atom, a halogen atom or an ordinary leaving group of organic chemistry, to lead to the compounds of the formula (IV/a):

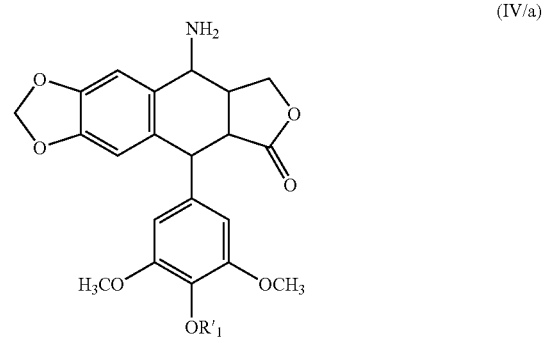

(IV/a)

wherein R'$_1$ is such as defined previously,
or to the action of a compound of the formula (V):

G-L  (V)

wherein G represents a traditional protective group of hydroxy functions and L an ordinary leaving group of organic chemistry, to lead to the compounds of the formula (IV/b):

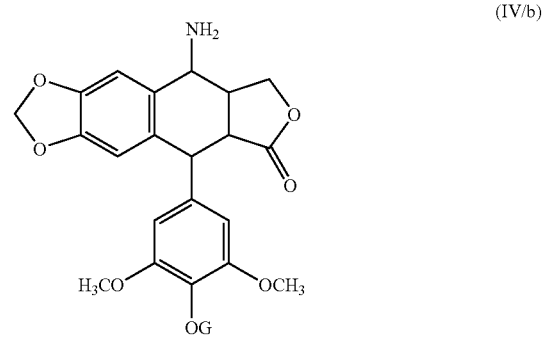

(IV/b)

wherein G is such as defined previously,
the whole of the compounds of the formula (IV/a) and (IV/b) forming the compounds of the formula (IV):

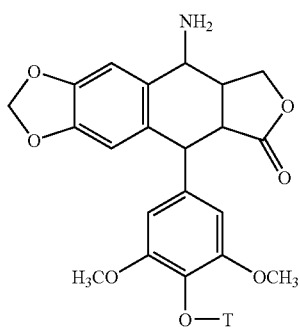

(IV)

wherein T represents an R'₁ group or G such as previously defined, a compound of the formula (IV), which is subjected, under basic conditions, to the action of a compound of the formula (VI):

R'₃—X'  (VI)

wherein R'₃ represents a group chosen among straight or branched $(C_1-C_6)$alkyl, cycloalkyl, straight or branched $(C_1-C_6)$cycloalkylalkyl, aryl or straight or branched $(C_1-C_6)$arylalkyl, and X' represents a hydrogen atom, a halogen atom or an ordinary leaving group of organic chemistry, to lead to the compounds of the formula (VII):

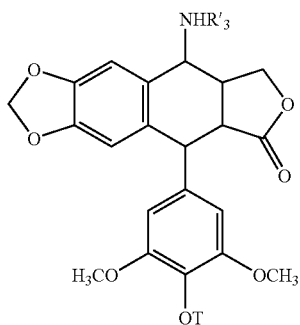

(VII)

wherein R'₃ and T are such as previously defined, the whole of the compounds of the formulas (IV) and (VII) forming the compounds of the formula (VIII):

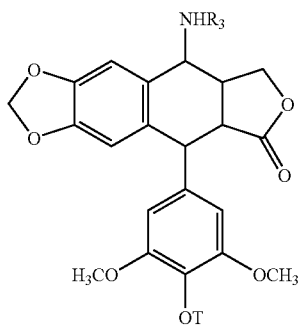

(VIII)

wherein $R_3$ is defined as in claim 1 and T is as defined previously, a compound of the formula (VIII) which are treated in a basic medium by a compound of the formula (IX):

(IX)

wherein Y and $R_4$ are such as defined in the formula (I) in claim 1, and Hal represents a halogen atom, to lead to the compounds of the formulas (I/a) and (I/b), specific cases of the compounds of the formula (I), according to whether T represents an R'₁ group or G, respectively:

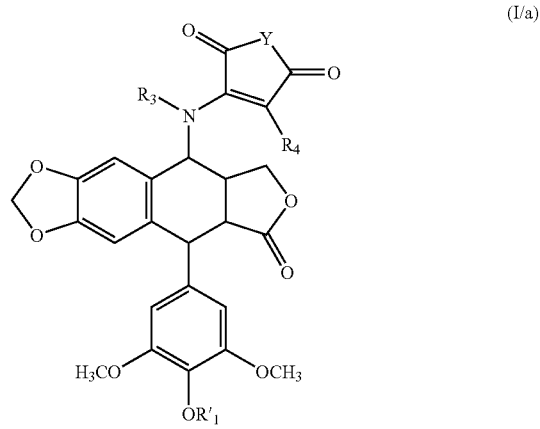

(I/a)

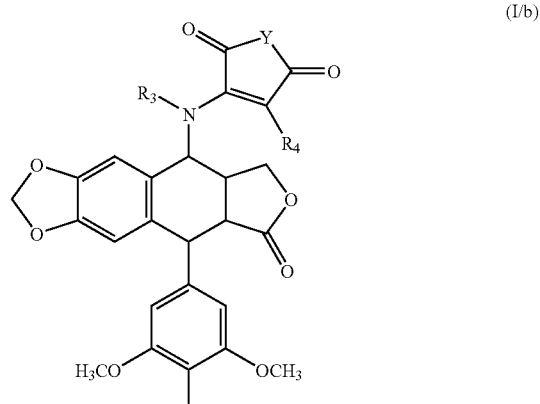

(I/b)

wherein R'₁ and G are as defined previously, $R_3$, $R_4$, and Y are such as previously defined in claim 1, a compound of the formula (I/b) wherein the hydroxy function is deprotected according to the traditional methods of organic chemistry, to lead to the compounds of the formula (I/c), specific cases of the compounds of the formula (I):

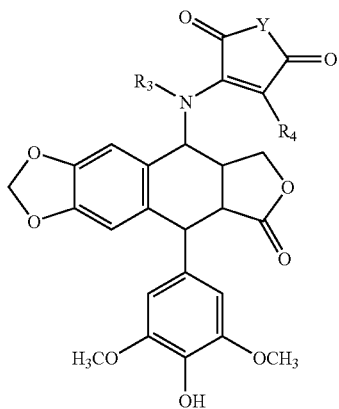

(I/c)

wherein $R_3$, $R_4$ and Y are such as previously defined in claim 1, the compounds (I/a) to (I/c) form the whole of the compounds of the invention, which can be purified, if necessary, according to a traditional purification technique, which can, if it is desired, be separated into the various optical isomers thereof according to a traditional separation technique, and which can be transformed, if it is desired, into the addition salts thereof to a pharmaceutically acceptable acid or base.

11. Pharmaceutical compositions containing as an active ingredient at least one compound according to claim 1, alone or in combination with one or more nontoxic, inert, pharmaceutically acceptable excipients or vehicles.

12. Method for treating cancer comprising the administration of an effective amount of a pharmaceutical composition according to claim 11 to a patient in need thereof.

13. The compound according to claim 1, wherein the heteroaryl group is selected from the group consisting of pyridyl, pyrrolyl, thienyl, furyl, pyrazinyl, isothiazolyl, thiazolyl, oxazolyl, isoxazolyl, pyrimidinyl, indolyl, benzofuranyl, benzothienyl, quinolyl, isoquinolyl, benzo [1,4]dioxynyl, and 2,3-dihydrobenzo [1,4]dioxynyl;

the cycloalkyl group is selected from the group consisting of cyclopropyl, cyclobutyl, cyclopentyl, and cyclohexyl; and the heterocycloalkyl group is selected from the group consisting of piperidyl, piperazinyl, and morpholyl.

* * * * *